United States Patent
Strobl et al.

[11] Patent Number: 5,820,547
[45] Date of Patent: Oct. 13, 1998

[54] ENDOSCOPE OPTICS TESTER

[75] Inventors: Karlheinz Strobl, Fiskdale; Eugene A. Antoine, Jr., Framingham, both of Mass.

[73] Assignee: Karl Storz GmbH & Co., Tuttlingen, Germany

[21] Appl. No.: 719,325

[22] Filed: Sep. 25, 1996

[51] Int. Cl.$^6$ .............................. A61B 1/00; H04N 17/00
[52] U.S. Cl. ........................ 600/127; 600/117; 348/188
[58] Field of Search ...................................... 600/101, 102, 600/117, 127, 175; 348/187, 188, 71, 75, 65; 359/630, 110; 356/304, 243; 283/115

[56] References Cited

U.S. PATENT DOCUMENTS

| | | | |
|---|---|---|---|
| 4,575,124 | 3/1986 | Morrison | 348/188 |
| 4,628,342 | 12/1986 | Desmons et al. | 348/188 |
| 4,761,685 | 8/1988 | Asaida et al. | 348/188 |
| 5,142,359 | 8/1992 | Yamamori | 348/188 |

*Primary Examiner*—John P. Leubecker
*Attorney, Agent, or Firm*—Donald D. Mon

[57] ABSTRACT

A portable endoscope tester determines specific properties of an endoscope optical system and enables comparisons between individual endoscopes to be made. The tester includes a holder for receiving and aligning an endoscope and a target attachable to the holder. The target is held in a plane normal to the optical axis of the endoscope when received in the holder. Opaque indicia indicative of the optical properties of the endoscope appears on the target and include a central disk with either a pinhole or a cross formed at the center, a plurality of field circles including an inner and outer bold ring, an inner and outer group of resolution targets arranged at respective clock positions, each resolution target comprising a plurality of parallel lines of different width and spacing, and rectangular grid centered on the optical axis. Depth of field, magnification, clarity, resolution, tilted de-centered optical color fringing, field and direction of view, coma and fall-off of resolution from the center to the edge can be detected.

10 Claims, 2 Drawing Sheets

ENDOSCOPE OPTICS TESTER

SPECIFICATION

1. Field of the Invention

This invention relates to the testing, appraisal, and comparison of endoscopes.

2. Background of the Invention

The heart of an endoscopic system is in its endoscope. There are two optical types—those which utilize lenses for image forwarding and formation, and those which utilize fiber optic bundles for forwarding the image. The former is usually referred to as a "rigid" endoscope, and the latter as a "flexible" endoscope. In all cases, the elements of the endoscope are carefully installed and aligned by the manufacturer so as to present the best image to the ocular piece, or to the camera, as possible.

The performance characteristics of the individual endoscope are of immediate and very intimate importance to the surgeon. It is important for the surgeon to be aware, before the procedure, that the endoscope can inherently deliver the quality of image he requires, and that if it inherently has such quality, the instrument is in good enough condition that it can deliver that quality.

Depending on the inherent design of the endoscope, the specific instrument might not provide the magnification, clarity, depth of field and resolution which would be required, even if it appears undamaged from a cursory inspection.

Then it is an unfortunate fact that actions apart from its actual use in the patient such as handling, transporting and cleaning, the endoscope may have become misaligned or otherwise damaged. A resulting inability to resolve an area of the field should not first be discovered by the surgeon while the endoscope is inserted in the patient during an endoscopic procedure, as this may result in adverse consequences including additional surgery costs, surgery cancellations and increased risk to the patient.

It is an object of this invention to provide a simple and portable tester, conveniently usable in the field, to determine specific properties of an endoscope, and to enable comparisons between individual endoscopes to be made. With this device, both on and off-axis resolution can be determined both qualitatively and quantitatively for a given combination of magnifications and detector (such as a CCD camera).

In addition, by utilizing the appropriate targets defects in the instrument such as depth of field, optional elements, tilted de-centered optical color fringing, field of and direction of view, coma, and fall-off of resolution from the center to the edge of the image can be detected, and if necessary assessed.

It is another object of this invention to provide means for making a meaningful comparison between endoscopes of the same design, and between endoscopes of different design from one to another.

BRIEF DESCRIPTION OF THE INVENTION

A tester according to this invention includes a holder. The holder supports a target and an endoscope.

The holder is adapted to receive and position an endoscope so that the axis of the direction of view of the endoscope is directed to the center of the target. The plane of the target is normal to the direction of view of the image.

According to a preferred feature of the invention, in the case where the target plane is normal to the direction of view the target includes a central pattern having a center opaque disk, preferably black, with a cross, preferably white, or a pinhole through the target, an inner bold ring of known diameter, and between the bold ring and the disc, and a first sequential group of resolution targets.

An outer bold ring is concentric with the inner ring and spaced from it. A second sequential group of resolution targets extends circularly just inside the outer ring.

According to a preferred but optional feature of the invention, the resolution targets are provided in discrete segments, each with a characteristic different line width and line separation.

According to yet another optional feature of the invention, the target is provided with a concentric group of rings each of which corresponds to a change of field of view of approximately 10 degrees at a specified target distance, and a group of horizontal and vertical straight grid lines is provided to aid in detection of distortion.

According to still another optional feature of the invention, a grid comprising two groups of horizontal and vertical double lines enable the testing of resolution variation across the field.

The above and other features of this invention will be fully understood from the following detail description and the accompanying drawings in which:

DETAILED DESCRIPTION OF THE INVENTION

Figure 1:
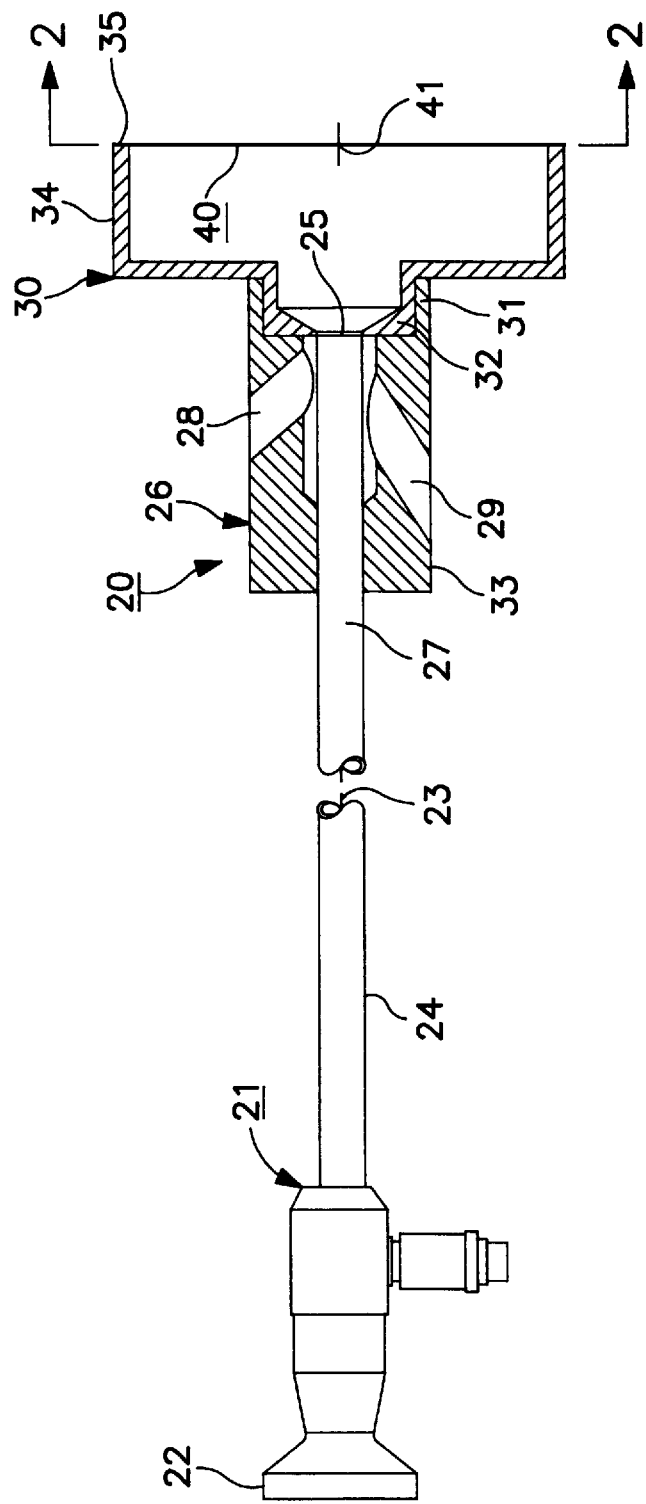
FIG. 1 is a side view, partly in cutaway cross section showing the presently preferred embodiment of the invention.
Figure 2:
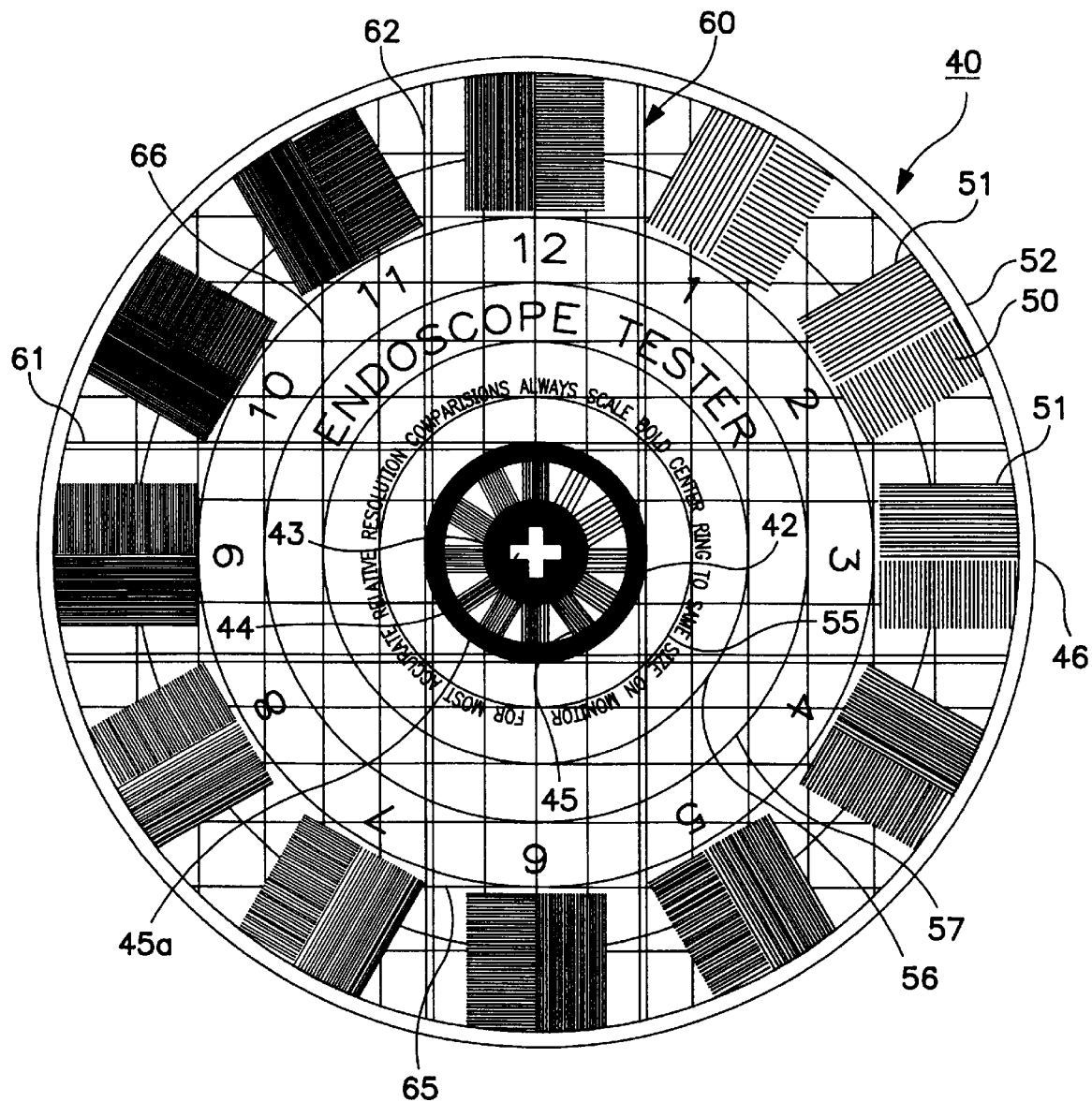
FIG. 2 is a view taken at line 2—2 in FIG. 1.

The presently preferred embodiment of an endoscope tester 20 is shown in FIGS. 1 and 2. Its purpose is the assess the optical properties of an endoscope 21. Typically an endoscope has an eye piece 22 (or a connection to another imaging device such as a CCD camera. It has a central axis 23 relative to an optical system (not shown) inside a shaft 24. The shaft will often include its own illuminating means. The distal end 25 of the endoscope is inserted into a surgical situs during surgical procedures.

A holder 26 has an axial port 27 to receive and align the endoscope. This port is used for zero degree endoscopes. There also exist side-viewing endoscopes, for which ports 28, 29 are provided to receive and align such endoscopes at a respective angle relative to the central axis, such as 30 degrees and 45 degrees.

An adapter 30 includes a neck 31 insertable into a socket 32 in the body 33 of the holder. A spacer segment 34 terminates at a rim 35 to which a target 40 is applied. It is held normal to the axis of the system, and at a proper spacing from the endoscope. This spacing is adjustable as required to match the field of view angle to the appropriate target distance allowing visualization of the entire target.

Target 40 is most conveniently made of a flat rigid sheet of material. If the pattern is to be back-lit, the material should be transparent, or at least sufficiently translucent. It may be front lit by the endoscope illumination system, or lit externally from the back as preferred. Front lit targets should have a non-reflective finish to reduce glare.

The presently preferred embodiment of target, though not optimized for depth of field is shown in FIG. 2, where the various indicia are provided as opaque shapes. The target will be round, concentric with its center 41 which will be located on axis 24.

A central pattern 42 includes an opaque center disk 43. At its center there is a central hole through the target (not shown, for back lit applications) or a white cross 44 for front or back lit usage. An inner bold ring 45a has a diameter greater than the disk, leaving an annular spacing 45 between them.

In annular spacing 45 there is placed a sequential group 46 of resolution targets. These targets differ importantly from one another. Both as a convenience in use, and for another purpose to be discussed below, they are identified by clock position indicia 1 through 12, each one being 30 degrees from the next. Both the resolution targets and these numbers will also be presented in opaque colors, preferably black.

These targets 46 each comprise segments made of line pairs (about 50% white and about 50% black) having line spacings according to the following table:

| clock position | resolution lines/mm | size (inches) |
| --- | --- | --- |
| 1 | 2.2 | 0.008948 |
| 2 | 2.6 | 0.007571 |
| 3 | 3.2 | 0.006152 |
| 4 | 3.6 | 0.005468 |
| 5 | 4 | 0.004921 |
| 6 | 4.3 | 0.004578 |
| 7 | 4.6 | 0.004279 |
| 8 | 5 | 0.003937 |
| 9 | 5.6 | 0.003515 |
| 10 | 6.3 | 0.003125 |
| 11 | 8 | 0.002461 |
| 12 | 10 | 0.001969 |

A second sequence 50 of segments 51 of resolution targets are formed just inside of, and adjacent to a second bold ring 52. These are located symmetrically with targets 46 and have the same properties.

A group of circles 55, 56, 57 have increasing diameters respective to about 10 degrees of differing field angles, at a specified target distance.

Grid 60 is comprised of a set of horizontal lines 61 and vertical lines 62. Each of these lines is comprised of a pair of lines of resolution (two black lines separated by a white line)—testing resolution across its entire field of view. They can be observed for variations in resolution across the tester.

In addition, horizontal lines 65 and vertical lines 66 can provide distortion information (as can grid 60).

It will be observed that as the clock number increases, so the resolution, and the spacing between lines decreases. Thus, a determination may be made prior to surgery of the resolution which will be achieved by the endoscope. Both the inner and outer sequences provide this information, at their respective positions in the field. In the drawings, the lines in some of the segments are so numerous and small that they cannot accurately be shown in drawings of the size required for this patent application. Apart from this, the target is shown substantially to scale.

The dark indicia are opaque. The remainder of the target may be transparent, translucent, or a non-reflective white color.

The assembled length of holder and adapter is about 3.92 inches. The length of the center port in the adapter is about 1.77 inches. The diameter of the adapter port is about 1.00 inches, as in the effective diameter of the target, which fits across the adapter.

In use, the center disk is used to set the focus for a given target magnification. If a back lit pin hole is used, one can quickly determine whether there is an astigmatism or tilt problem. For example, if there had been a lens shift, one will see a bright center spot with some portion of a thin ring (halo or coma) around the bright center spot. When a cross is used, distortions or fuzziness of the edges of the cross will be seen under these circumstances, though this phenomenon is not as striking as the effect seen when utilizing the pin hole.

The bold ring is used to equalize the total system magnification of different endoscopes in order to make quantitative comparison of different endoscopes, because their center magnifications and the resolution of their detection systems will then be the same. For the comparison to be valid the orientation of all components used must be the same, with the exception of the different endoscopes to be tested.

The grids of rectangularly oriented lines give an indication of distortion and resolution across the entire field.

By monitoring the borders of the bold lines and clock numbers, one can observe color separations.

Depth of field characteristics can be observed by placing the target at an oblique angle to the direction of view of the endoscope.

This invention is not to be limited by the embodiment shown in the drawings and described in the description, which is given by way of example and not of limitation, but only in accordance with the scope of the appended claims.

We claim:

1. A tester for endoscopes comprising:
    a holder for receiving and aligning an endoscope, said holder having at least one port having an axis for receiving the distal end of an endoscope; and
    a target attachable to said holder, said target being planar, its plane being held by said holder normal to said axis, and at a predetermined location in said holder relative to said port, said target bearing opaque indicia indicative of optical properties of the endoscope, comprising a central disk, an inner bold ring of known diameter, and between said disk and inner bold ring a first sequential group of resolution targets, an outer bold ring concentric with said inner bold ring and spaced from it, and a second group of resolution targets extending circularly inside and adjacent to said outer bold ring, said groups of resolution targets each including increments at respective clock positions, each increment comprising a plurality of parallel lines of known width and spacing, the number of lines per millimeter increasing from increment to increment, and the spacing between them decreasing from increment to increment, whereby to provide successive regions respective of increasing resolution as the clock position increases.

2. A tester according to claim 1 in which said increments in said second group of resolution targets include a second set of like lines which extend normal to a radius from the center of the target.

3. A tester according to claim 1 in which a pin hole pierces the target at its center.

4. A tester according to claim 1 in which a white cross is formed at the center of the disk.

5. A tester according to claim 1 in which opaque clock numbers from 1 through 12 are placed inside of and adjacent to respective increments of said second group of resolution targets.

6. A tester according to claim 1 in which a rectangular grid comprised of a pair of spaced apart lines is centered on said axis, each of said lines comprising a pair of closely spaced-apart lines to provide an indication of variation of resolution over the field of the endoscope.

7. A tester according to claim 1 in which a plurality of field circles is formed around said axis at intervals respective to ten degree variations in the field of view of the endoscope.

8. A tester according to claim 1 in which said holder includes multiple ports, each disposed at a respective angle to said axis and intersecting said at least one port to receive endoscopes having respective off-axis viewing orientations.

9. A tester according to claim 1 in which a receptacle is formed in said holder to receive and to hold said target.

10. A tester according to claim 1 in which said target is at least translucent, to provide for backlighting of said target.

\* \* \* \* \*